United States Patent
Nowak et al.

(10) Patent No.: US 11,401,260 B2
(45) Date of Patent: Aug. 2, 2022

(54) BIOCHEMICAL BINDING OF RET9 AND VEGFR2 INHIBITORS

(71) Applicant: Kala Pharmaceuticals, Inc., Watertown, MA (US)

(72) Inventors: Pawel Wojciech Nowak, Woodcliff, NJ (US); Winston Z. Ong, Stoneham, MA (US)

(73) Assignee: Kala Pharmaceuticals, Inc., Arlington, MA (US)

( * ) Notice: Subject to any disclaimer, the term of this patent is extended or adjusted under 35 U.S.C. 154(b) by 161 days.

(21) Appl. No.: 16/757,305

(22) PCT Filed: Oct. 19, 2018

(86) PCT No.: PCT/US2018/056751
§ 371 (c)(1),
(2) Date: Apr. 17, 2020

(87) PCT Pub. No.: WO2019/079747
PCT Pub. Date: Apr. 25, 2019

(65) Prior Publication Data
US 2021/0179582 A1 Jun. 17, 2021

Related U.S. Application Data

(60) Provisional application No. 62/575,280, filed on Oct. 20, 2017.

(51) Int. Cl.
*C07D 401/14* (2006.01)
*A61K 31/517* (2006.01)
*A61K 9/00* (2006.01)

(52) U.S. Cl.
CPC .......... *C07D 401/14* (2013.01); *A61K 9/0048* (2013.01); *C07B 2200/05* (2013.01)

(58) Field of Classification Search
CPC ........................... C07D 401/14; A61K 31/517

USPC ...................................... 544/284; 514/266.21
See application file for complete search history.

(56) References Cited

U.S. PATENT DOCUMENTS 7,074,800 B1 * 7/2006 Stokes .................... A61P 37/02
514/266.3

* cited by examiner

*Primary Examiner* — Charanjit Aulakh
(74) *Attorney, Agent, or Firm* — K&L Gates LLP; Louis C. Cullman; Michelle Glasky Bergman

(57) ABSTRACT

Provided herein are compounds, compositions, and pharmaceutical compositions of Formula (I). Also provided herein are methods of using compounds of Formula (I) to treat proliferative diseases, ocular diseases, dermatological diseases, inflammatory diseases, autoimmune diseases, autoinflammatory diseases, and metabolic diseases. Also provided herein are methods of using the compounds of Formula (I) as therapeutics, e.g., in the treatment and/or prevention of diseases associated with growth factor activity or angiogenesis. In some embodiments, the disease being treated is a proliferative disease.

(I)

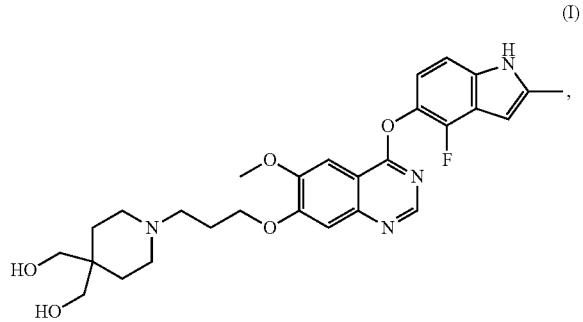

8 Claims, No Drawings

BIOCHEMICAL BINDING OF RET9 AND VEGFR2 INHIBITORS

CROSS REFERENCE TO RELATED APPLICATIONS

The present application is a national phase application of International Patent Application PCT/US2018/056751 filed Oct. 19, 2018, which claims the benefit of U.S. Provisional Patent Application 62/575,280, filed Oct. 20, 2017, the entire contents of both of which are incorporated by reference herein.

BACKGROUND

Growth factors play an important role in angiogenesis, lymphangiogenesis, and vasculogenesis. Growth factors regulate angiogenesis in a variety of processes including embryonic development, wound healing, and several aspects of female reproductive function. Undesirable or pathological angiogenesis is associated with diseases including diabetic retinopathy, psoriasis, cancer, rheumatoid arthritis, atheroma, Kaposi's sarcoma, and hemangioma. Angiogenic ocular conditions represent the leading cause of irreversible vision loss in developed countries. In the United States, for example, retinopathy of prematurity, diabetic retinopathy, and age-related macular degeneration are the principal causes of blindness in infants, working age adults, and the elderly, respectively. Efforts have been developed to promote angiogenesis in treatment of these conditions.

Accordingly, new therapeutic compounds are needed for the treatment of diseases associated with aberrant signaling of growth factors, such as cancer, macular degeneration, and diabetic retinopathy.

SUMMARY

Provided herein is a compound of Formula I:

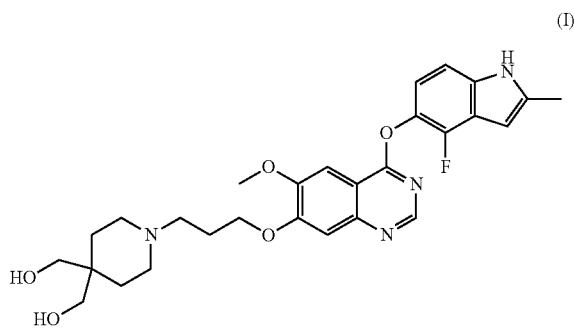 [SMILES: COc1cc2c(Oc3ccc4[nH]c(C)cc4c3F)ncnc2cc1OCCCN1CCC(CO)(CO)CC1]

(I)

or a solvate, a hydrate, a polymorph, a co-crystal, a prodrug, an N-oxide, or an isotopically labeled compound thereof, or a pharmaceutically acceptable salt thereof.

Also provided herein are compositions comprising the compound of Formula I or a solvate, a hydrate, a polymorph, a co-crystal, a prodrug, an N-oxide, or an isotopically labeled compound thereof, or a pharmaceutically acceptable salt thereof.

Also provided herein are pharmaceutical compositions, comprising the compound of Formula I or a solvate, a hydrate, a polymorph, a co-crystal, a prodrug, an N-oxide, or an isotopically labeled compound thereof, or a pharmaceutically acceptable salt of any of the foregoing (collectively, the "Pharmaceutical Molecules").

Also provided herein are methods of treating an ocular disease in a subject in need thereof, comprising administering to the subject a therapeutically effective amount of the Pharmaceutical Molecules.

Also provided herein are methods of treating an ocular disease in a subject in need thereof, comprising administering to the subject a therapeutically effective amount of the compositions provided herein.

Also provided herein are methods of treating an ocular disease in a subject in need thereof, comprising administering to the subject a therapeutically effective amount of the pharmaceutical compositions provided herein.

Also provided herein are kits, comprising:
(a) the compound of Formula I or a solvate, a hydrate, a polymorph, a co-crystal, a prodrug, an N-oxide, or an isotopically labeled compound thereof, or a pharmaceutically acceptable salt thereof; and
(b) instructions for use thereof.

Also provided herein are kits, comprising:
(a) a composition provided herein; and
(b) instructions for use thereof.

Also provided herein are kits, comprising:
(a) a pharmaceutical composition provided herein; and
(b) instructions for use thereof.

In some embodiments, the kits provided herein include a single dose or multiple doses of a compound, composition, or pharmaceutical composition provided herein. The provided kits may be useful for the treatment of proliferative diseases, ocular diseases, dermatological diseases, inflammatory diseases, autoimmune diseases, autoinflammatory diseases, and metabolic diseases. In some embodiments, the kits further include packaging information describing the use or prescribing information for the subject or a health care professional. Such information may be required by a regulatory agency such as the U.S. Food and Drug Administration (FDA). The kit may also optionally include a device for administration of the compound or composition, for example, a dropper for ocular administration or a syringe for parenteral administration.

Also provided herein are methods of treating proliferative diseases, ocular diseases, dermatological diseases, inflammatory diseases, autoimmune diseases, autoinflammatory diseases, or metabolic diseases, comprising administering to the subject a therapeutically effective amount of a Pharmaceutical Molecule.

Also provided herein are methods of treating proliferative diseases, ocular diseases, dermatological diseases, inflammatory diseases, autoimmune diseases, autoinflammatory diseases, or metabolic diseases, comprising administering to the subject a therapeutically effective amount of a composition provided herein.

Also provided herein are methods of treating proliferative diseases, ocular diseases, dermatological diseases, inflammatory diseases, autoimmune diseases, autoinflammatory diseases, or metabolic diseases, comprising administering to the subject a therapeutically effective amount of a pharmaceutical composition provided herein.

Also provided herein are methods of preventing proliferative diseases, ocular diseases, dermatological diseases, inflammatory diseases, autoimmune diseases, autoinflammatory diseases, or metabolic diseases, comprising administering to the subject a therapeutically effective amount of a Pharmaceutical Molecule.

Also provided herein are methods of preventing proliferative diseases, ocular diseases, dermatological diseases, inflammatory diseases, autoimmune diseases, autoinflammatory diseases, or metabolic diseases, comprising administering to the subject a therapeutically effective amount of a composition provided herein.

Also provided herein are methods of preventing proliferative diseases, ocular diseases, dermatological diseases, inflammatory diseases, autoimmune diseases, autoinflammatory diseases, or metabolic diseases, comprising administering to the subject a therapeutically effective amount of a pharmaceutical composition provided herein.

Also provided herein are methods of using a Pharmaceutical Molecule to study the inhibition of growth factor signaling.

Also provided herein are methods of using a composition provided herein to study the inhibition of growth factor signaling.

Also provided herein are methods of using a pharmaceutical composition provided herein to study the inhibition of growth factor signaling.

Also provided are methods of treating disorders associated with aberrant growth factor signaling comprising administering to a subject a therapeutically effective amount of a compound, composition, or pharmaceutical composition provided herein.

The compounds, compositions, and pharmaceutical compositions provided herein are particularly useful in treating diseases associated with angiogenesis.

In some embodiments, the Pharmaceutical Molecules provided herein may be intended for delivery in a subject's tissues having mucus (e.g., eye, respiratory tract, gastrointestinal tract, genito-urinary tract), which is a viscoelastic and adhesive substance that traps most foreign objects (e.g., microorganisms, particles, dust). In some embodiments, the Pharmaceutical Molecules are modified or coated with a coating. In some embodiments, such coating can reduce the mucoadhesiveness, and/or reduce the size of particles of the Pharmaceutical Molecules.

Also provided herein are Pharmaceutical Molecules formulated into mucus penetrating particles (MPPs) suitable for administration (e.g., topical or inhalation) to tissues of the subject having mucus (e.g., eye, respiratory tract, gastrointestinal tract, genito-urinary tract). In some embodiments, the Pharmaceutical Molecules are crystalline.

Also provided herein is a plurality of particles comprising a Pharmaceutical Molecule provided herein. In certain embodiments, the particles are mucus penetrating. In some embodiments, each of such particles comprises a core particle and a coating surrounding a core particle. In some embodiments, the core particle comprises a Pharmaceutical Molecule described herein, or the core particle comprises a polymeric core with the Pharmaceutical Molecule encapsulated in a polymer. In some embodiments, the core particle comprise at least about 50%, at least about 60%, at least about 70%, at least about 80%, at least about 85%, at least about 90%, at least, about 95%, at least about 96%, at least about 97%, at least about 98%, at least about 99%, at least about 99.5%, at least about 99.9% by weight of a Pharmaceutical Molecule provided herein. In some embodiments, the core particle consists essentially of a Pharmaceutical Molecule or comprises about 100% by weight of a Pharmaceutical Molecule. In certain embodiments, the particles are nanoparticles (e.g., particles having an average diameter of at least about 10 nm and less than about 1 μm). The particles may be useful in delivering the Pharmaceutical Molecules to a subject. In some embodiments, the particles provided herein are capable of delivering the Pharmaceutical Molecules in or through mucus of a subject.

Also provided herein are pharmaceutical compositions comprising a particle or a plurality of particles provided herein. In certain embodiments, the pharmaceutical compositions are useful in delivering a pharmaceutical agent (e.g., a compound provided herein) to a subject.

Also provided herein are pharmaceutical compositions comprising a plurality of particles comprising (i) a core particle comprising a Pharmaceutical Molecule provided herein, and (ii) a coating of a mucus penetration-enhancing surface altering agent surrounding the core particle, and optionally, at least one pharmaceutically acceptable excipient or carrier. In some embodiments, the mucus penetration-enhancing surface altering agent is present on the outer surface of the core particle at a density of at least 0.01 surface altering agents per $nm^2$. In some embodiments, the surface altering agent is a triblock copolymer of the structure (hydrophilic block)-(hydrophobic block)-(hydrophilic block). In some embodiments, the triblock copolymer is a PLURONIC® or poloxamer.

In some embodiments, the Pharmaceutical Molecules, particles, or pharmaceutical compositions are formulated to be mucus penetrating.

In some embodiments, the Pharmaceutical Molecule is: a compound of Formula (I),

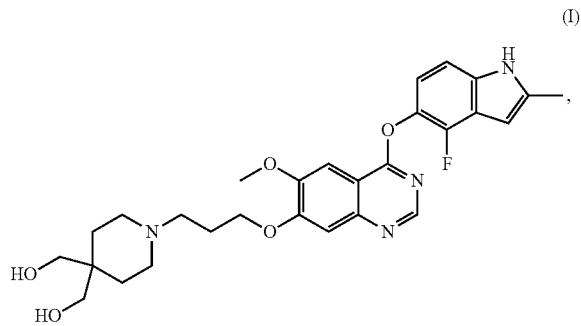 [SMILES: COc1cc2c(Oc3ccc4[nH]c(C)cc4c3F)ncnc2cc1OCCCN1CCC(CO)(CO)CC1]

or a solvate, a hydrate, a polymorph, a co-crystal, a prodrug, an N-oxide, or an isotopically labeled compound thereof, or a pharmaceutically acceptable salt thereof.

In some embodiments, the Pharmaceutical Molecule is a compound of Formula (I) or a pharmaceutically acceptable salt thereof, or a deuterated derivative thereof.

In some embodiments, the Pharmaceutical Molecule is a compound of Formula (I).

In some embodiments, the Pharmaceutical Molecule is a pharmaceutically acceptable salt of a compound of Formula (I).

In some embodiments, the Pharmaceutical Molecule is a deuterated derivative of: a compound of Formula (I) or a pharmaceutically acceptable salt thereof.

In some embodiments, the Pharmaceutical Molecule is an isotopically labeled compound of, such as a deuterated derivative of: a compound of Formula (I) or a pharmaceutically acceptable salt thereof.

In some embodiments, the Pharmaceutical Molecule is a solvate or a hydrate of a compound of Formula (I) or a pharmaceutically acceptable salt thereof.

In some embodiments, the Pharmaceutical Molecule is a co-crystal of a compound of Formula (I) or a pharmaceutically acceptable salt thereof.

In some embodiments, the Pharmaceutical Molecule is crystalline.

DETAILED DESCRIPTION

Provided herein are a compound of Formula (I):

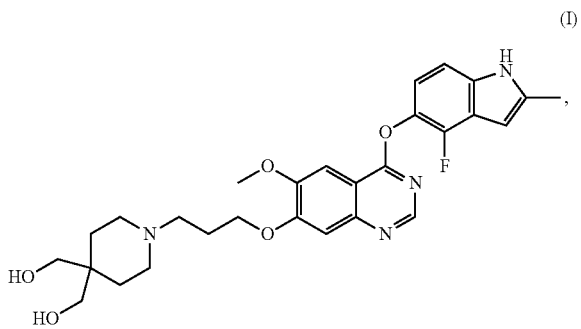 [SMILES: COc1cc2c(Oc3ccc4[nH]c(C)cc4c3F)ncnc2cc1OCCCN1CCC(CO)(CO)CC1]

(I)

a solvate, a hydrate, a co-crystal, a prodrug, an N-oxide, an isotopically labeled compound any of such compound of Formula (I), solvate, hydrate, co-crystal, prodrug, and N-oxide, and a pharmaceutically acceptable salt of any of the foregoing. It is noted that any of such compound of Formula (I), solvate, hydrate, co-crystal, prodrug, N-oxide, isotopically labeled compound and pharmaceutically acceptable salt can be in any form, such as crystalline, polymorphic, or an amorphous form. Also provided herein are methods of using compounds of Formula (I) to treat proliferative diseases, ocular diseases, dermatological diseases, inflammatory diseases, autoimmune diseases, autoinflammatory diseases, and metabolic diseases. Also provided herein are methods of using the compounds of Formula (I) as therapeutics, e.g., in the treatment and/or prevention of diseases associated with growth factor activity or angiogenesis. In some embodiments, the disease being treated is a proliferative disease. Exemplary proliferative diseases include, but are not limited to, cancers, benign neoplasms, diseases associated with angiogenesis, inflammatory diseases, autoinflammatory diseases, and autoimmune diseases. In certain embodiments, the disease is an ocular disease. Exemplary ocular diseases include, but are not limited to, macular degeneration (such as age-related macular degeneration (AMD) or dry- or wet-AMD), dry eye syndrome, uveitis, allergic conjunctivitis, glaucoma, and rosacea. In some embodiments, the methods are for treating ocular disease. In some embodiments, the methods are for treating macular degeneration. In some embodiments, the methods are for treating wet macular degeneration. In some embodiments, the methods are for wet age-related macular degeneration.

Definitions

Listed below are definitions of various terms used to describe this disclosure. These definitions apply to the terms as they are used throughout this specification and claims, unless otherwise limited in specific instances, either individually or as part of a larger group.

The term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The terms "administer," "administering," or "administration," as used herein refers to implanting, absorbing, ingesting, injecting, inhaling, or otherwise introducing an inventive compound, or a pharmaceutical composition thereof.

The term "angiogenesis" refers to the formation and growth of new blood vessels. Normal angiogenesis occurs in the body of a healthy subject during wound healing and for restoring blood flow to tissues after injury. The body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can result in new blood vessels that feed diseased tissues and/or destroy normal tissues, and in the case of cancer, the new vessels can allow tumor cells to escape into the circulation and lodge in other organs (tumor metastases).

As used herein, an "autoimmune disease" refers to a disease arising from an inappropriate immune response in the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppressants, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), uveitis, Sjögren's syndrome, Crohn's disease, Reiter's syndrome, ankylosing spondylitis, Lyme arthritis, Guillain-Barre syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

A "biocompatible" material refers to a material that does not typically induce an adverse response when inserted or injected into a subject. The adverse response includes significant inflammation and/or acute rejection of the material by the immune system of the subject, for instance, via a T-cell-mediated response. It is recognized that "biocompatibility" is a relative term and that some degree of immune response is to be expected even for materials that are highly compatible with living tissues of the subject. However, as used herein, "biocompatibility" refers to the acute rejection of a material by at least a portion of the immune system, i.e., a material that lacks biocompatibility (i.e. being non-biocompatible) in a subject provokes an immune response in the subject that is severe enough such that the rejection of the material by the immune system cannot be adequately controlled and often is of a degree such that the material must be removed from the subject in order for the subject to be as well as it was before the non-biocompatible material was introduced into the subject. One test to determine biocompatibility of a material is to expose the material to cells (e.g., fibroblasts or epithelial cells) in vitro; the material is considered biocompatible if it does not result in significant cell death at moderate concentrations, e.g., at concentrations of about 50 micrograms/$10^6$ cells. In certain embodiments, there is no significant cell death if less than about 20% of the cells are dead, even if phagocytosed or otherwise taken up by the cells. In some embodiments, a material is biocompatible if contacting it with cells in vitro results in less than 20% cell death and if the administration of the material in vivo does not induce unwanted inflammation or other adverse responses. In certain embodiments, a biocompatible material is biodegradable. A non-limiting example of biocompatible materials is biocompatible polymers (including biocompatible copolymers).

A "biodegradable" material refers to a material that is able to degrade chemically and/or biologically (e.g., by hydrolysis or enzymatic activity), within a physiological environment, such as within the body or when introduced to cells. For instance, the material may be one that hydrolyzes spontaneously upon exposure to water (e.g., within a subject) and/or may degrade upon exposure to heat (e.g., at temperatures of about 37° C.). Degradation of a material may occur at varying rates, depending on the material used. For example, the half-life of the material (the time at which 50% of the material is degraded into smaller components) may be on the order of days, weeks, months, or years. The material may be biologically degraded, e.g., by enzymatic activity or cellular machinery, for example, through exposure to a lysozyme. In some embodiments, the material may be broken down into smaller components that cells can either reuse or dispose of without significant toxic effect on the cells (e.g., fewer than about 20% of the cells are killed when the components are added to cells in vitro). Non-limiting examples of biodegradable materials are biodegradable polymers (including biodegradable copolymers). Examples of biodegradable polymers include, but are not limited to, poly(ethylene glycol)-poly(propylene oxide)-poly(ethylene glycol) triblock copolymers, poly(vinyl alcohol) (PVA), poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters), and copolymers thereof (e.g., poly(lactide-co-glycolide) (PLGA)).

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

As used herein, the term "cancer" refers to a malignant neoplasm. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor; germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (e.g., B-cell NHL such as diffuse large cell lymphoma (e.g., diffuse large B-cell lymphoma), follicular lymphoma, chronic lymphocytic leukemia/small lymphocytic lymphoma, mantle cell lymphoma, marginal zone B-cell lymphomas (e.g., mucosa-associated lymphoid tissue lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia, immunoblastic large cell lymphoma, precursor B-lymphoblastic lymphoma and primary central nervous system lymphoma; and T-cell NHL such as precursor T-lymphoblastic lymphoma/leukemia, peripheral T-cell lymphoma (e.g., cutaneous T-cell lymphoma (e.g., mycosis fungiodes, Sézary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer, malignant hepatoma); lung cancer (e.g., bronchogenic carcinoma, small cell lung cancer, non-small cell lung cancer, adenocarcinoma of the lung); leiomyosarcoma; mastocytosis (e.g., systemic mastocytosis); muscle cancer; myelodysplastic syndrome; mesothelioma; myeloproliferative disorder (e.g., polycythemia vera, essential thrombocytosis, agnogenic myeloid metaplasia a.k.a. myelofibrosis, chronic idiopathic myelofibrosis, chronic myelocytic leukemia, chronic neutrophilic leukemia, hypereosinophilic syndrome); neuroblastoma; neurofibroma (e.g., neurofibromatosis type 1 or type 2, schwannomatosis); neuroendocrine cancer (e.g., gastroenteropancreatic neuroendoctrine tumor, carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm, Islet cell tumors); penile cancer (e.g., Paget's disease of the penis and scrotum); pinealoma; primitive neuroectodermal tumor; plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma, keratoacanthoma, melanoma, basal cell carcinoma); small bowel cancer (e.g., appendix cancer); soft tissue sarcoma (e.g., malignant fibrous histiocytoma, liposarcoma, malignant peripheral nerve sheath tumor, chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma, medullary thyroid cancer); urethral cancer; vaginal cancer; vulvar cancer (e.g., Paget's disease of the vulva); multiple endocrine neoplasia type 2A; multiple endocrine neoplasia type 2B; pheochromocytoma; and parathyroid hyperplasia.

As used herein, the terms "condition," "disease," and "disorder" are used interchangeably.

The terms "crystalline" or "substantially crystalline," when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. It can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein. The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal. When not used with respect to a nanostructure, the term "monocrystalline" to materials that are composed of substantially a single crystallite of substantially the same size and orientation.

As used herein, "deuterated derivative(s)" refers to a derivative of a parent compound, wherein the parent compound has been derivatized by replacing each of one or more hydrogen atoms with a deuterium atom. As such, the parent compound and the deuterated derivative(s) thereof have the same chemical structure except that one or more hydrogen atoms of the parent compound are replaced by a deuterium atom(s) in the deuterated derivative(s).

An "effective amount" of a compound provided herein refers to an amount sufficient to elicit a desired biological response, i.e., treating the condition. As will be appreciated by those of ordinary skill in this art, the effective amount of a compound provided herein may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor. In treating macular degeneration, an effective amount of an inventive compound may improve sight, reduce the risk of vision loss, or prevent central vision loss from worsening.

As used herein, the term "growth factor-associated disease" means any disease where growth factors are known to play a role. Accordingly, in some embodiments, the present disclosure relates to treating diseases in which growth factors are known to play a role. Such diseases include proliferative diseases, eye diseases, dermatological diseases, inflammation diseases, and metabolic diseases.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrates, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica, gouty arthritis, degenerative arthritis, tendonitis, bursitis, psoriasis, cystic fibrosis, arthrosteitis, rheumatoid arthritis, inflammatory arthritis, Sjögren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis, asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome, encephalitis, immediate hypersensitivity reactions, asthma, hay fever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

The term "kinase" refers to any enzyme that catalyzes the addition of a phosphate group to a residue of a protein. For example, a serine kinase catalyzes the addition of a phosphate group to a serine residue of a protein.

The term "macular degeneration" refers to diseases that result from atrophy of the retinal pigment epithelial layer below the neurosensory retina, which causes vision loss through loss of photoreceptors (rods and cones) in the central part of the retinal. A macular degeneration includes, without limitation, an age related macular degeneration (AMD) (e.g., wet AMD or dry AMD).

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "microparticle" refers to a particle having a characteristic dimension of less than about 1 millimeter and at least about 1 micrometer, where the characteristic dimension of the particle is the smallest cross-sectional dimension of the particle.

A "nanocrystal" is a nanostructure. A nanocrystal thus has at least one region or characteristic dimension with a dimension of less than about 1000 nm, e.g., less than about 300 nm less than about 200 nm, less than about 100 nm, or less than about 50 nm. Typically, the region or characteristic dimension will be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, and the like. Nanostructures can be substantially homogeneous in material properties, or in certain embodiments can be heterogeneous (e.g. heterostructures). Optionally, a nanocrystal can comprise one or more surface ligands (e.g., surfactants). The nanocrystal is optionally substantially single crystal in structure (a "single crystal nanostructure" or a "monocrystalline nanostructure"). While nanostructures for use as described herein can be fabricated from essentially any convenient material or material, preferably the nanostructure is prepared from an inorganic material, e.g., an inorganic conductive or semiconductive material. A conductive or semi-conductive nanostructure often displays 1-dimensional quantum confinement, e.g., an electron can often travel along only one dimension of the structure. Nanocrystals can be substantially homogeneous in material properties, or in certain embodiments can be heterogeneous (e.g. heterostructures). The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals can be fabricated from essentially any convenient material or materials.

The term "nanoparticle" refers to a particle having a characteristic dimension of less than about 1 micrometer and at least about 1 nanometer, where the characteristic dimension of the particle is the smallest cross-sectional dimension of the particle. A crystalline nanoparticle is referred to as a "nanocrystal."

The term "nanostructure" refers to a structure having at least one region or characteristic dimension with a dimension of less than about 1000 nm, e.g., less than about 300 nm, less than about 200 nm, less than about 100 nm, or less than about 50 nm. Typically, the region or characteristic dimension will be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), and the like. Nanostructures can be substantially homogeneous in material properties, or in certain embodiments can be heterogeneous (e.g. heterostructures). Nanostructures can be, e.g., substantially crystalline, substantially monocrystalline, polycrystalline, amorphous, or a combination thereof. In one aspect, each of the three dimensions of the nanostructure has a dimension of less than about 1000 nm, e.g., or even less than about 300 nm, less than about 200 nm, less than about 100 nm, or less than about 50 nm. Nanostructures can comprise one or more surface ligands (e.g., surfactants).

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "ocular disease" or "ocular disorder" refers to any eye disease and/or disorder. For example, ocular diseases can be disorders of the eyelid, lacrimal system and orbit, disorders of conjunctiva, disorders of sclera, cornea, iris and ciliary body, disorders of choroid and retina, glaucoma, disorders of optic nerve and visual pathways, or disorders of ocular muscles. Additionally, ocular disease can also refer to discomfort following injury, surgery, or laser treatment. Diseases and disorders of the eye include, but are not limited to, macular degeneration, dry eye syndrome, uveitis, allergic conjunctivitis, glaucoma, and rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals. Uveitis or iridocyclitis refers to inflammation of the middle layer of the eye (the "uvea") and in common usage may refer to any inflammatory process involving the interior of the eye. Allergic conjunctivitis is inflammation of the conjunctiva (the membrane covering the white part of the eye) due to allergy. Glaucoma refers to a group of diseases that affect the optic nerve and involves a loss of retinal ganglion cells in a characteristic pattern, i.e., a type of optic neuropathy. Raised intraocular pressure is a significant risk factor for developing glaucoma (above 22 mmHg or 2.9 kPa), and inflammatory processes, e.g., uveitis, can cause this rise in intraocular pressure. Rosacea is a chronic inflammatory condition characterized by facial erythema but it can affect the eyes.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals (e.g., crystalline forms of compounds or active pharmaceutical agent), aggregates, composites, pulverized, milled, or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. For example, Table A of Berge et al. provides the following pharmaceutically acceptable salts:

TABLE A

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | Pantothenate |
| Esylate | Phosphate diphosphate | Polygalacturonate |
| Fumarate | Salicylate | Subacetate |
| Gluceptate | Stearate | Succinate |
| Gluconate | Sulfate | Tannate |
| Glutamate | Tartrate | Teociate |
| Glycollylarsanilate | Triethiodide | Hexylresorcinate |
| Hydrabamine | Hydrobromide | Hydrochloride |
| Hydroxynaphthoate | | |

Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carbonate, sulfate, phosphate, nitrate, lower alkyl sulfonate, and aryl sulfonate.

As used herein, the terms "pharmaceutical agent" and "drug" are used interchangeably.

As used herein, the terms "pharmaceutical composition" and "formulation" are used interchangeably.

The term "polycrystalline" refers to materials that are composed of many crystallites of varying size and orientation. When used with respect to nanostructures, the term "polycrystalline" refers to a crystalline nanostructure that is not monocrystalline.

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrug" refers to compounds, including derivatives of the compounds of Formula (I), which have cleavable groups and become by solvolysis or under physiological conditions the compounds provided herein which are pharmaceutically active in vivo. Such examples include, but are not limited to, choline ester derivatives and the like, N-alkylmorpholine esters and the like. Other derivatives of the compounds provided herein have activity in both their acid and acid derivative forms, but in the acid sensitive form often offers advantages of solubility, tissue compatibility, or delayed release in the mammalian organism (see, Bundgaard, Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds provided herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds provided herein may be preferred in certain instances.

A "proliferative disease" refers to a disease that occurs due to abnormal growth or extension by the multiplication of cells. A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

A "prophylactically effective amount" of a compound provided herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "protein" or "peptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

The term "RET" refers to a receptor tyrosine kinase of the RET proto-oncogene, and includes the three main isoforms of RET, which are RET51, RET43, and RET9. The natural alternative splicing of the RET gene results in the production of 3 different isoforms of the protein RET. RET51, RET43 and RET9 contain 51, 43 and 9 amino acids in their C-terminal tail respectively. RET is the receptor for glial cell line-derived neurotrophic factor (GDNF) family ligands.

As used herein, the term "RET-associated disease" means any disease where RET or an isoform thereof is known to play a role. Such diseases include various types of human cancer, including medullary thyroid carcinoma, multiple endocrine neoplasias type 2A and 2B, pheochromocytoma and parathyroid hyperplasia.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds provided herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

A "therapeutically effective amount" of a compound provided herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) provided herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The term "VEGF" is used interchangeably with vascular endothelial growth factor herein. VEGF includes, but is not limited to, VEGF-related proteins such as placenta growth factor (PIGF), VEGF-A, VEGF-B, VEGF-C, VEGF-D, VEGF-E, and VEGF-F. The term VEGF also covers a number of proteins from two families that result from alternate splicing of mRNA from a single, 8-exon, VEGF gene. The two different families are referred to according to their terminal exon (exon 8) splice site—the proximal splice site (denoted $VEGF_{xxx}$) or distal splice site ($VEGF_{xxxb}$). In addition, alternate splicing of exon 6 and 7 alters their heparin-binding affinity, and amino acid number (in humans: $VEGF_{121}$, $VEG_{121b}$, $VEGF_{145}$, $VEGF_{165}$, $VEGF_{165b}$, $VEGF_{189}$, $VEGF_{206}$; the rodent orthologs of these proteins contain one fewer amino acid). These domains have important functional consequences for the VEGF splice variants, as the terminal (exon 8) splice site determines whether the proteins are pro-angiogenic (proximal splice site, expressed during angiogenesis) or anti-angiogenic (distal splice site, expressed in normal tissues). In addition, inclusion or exclusion of exons 6 and 7 mediate interactions with heparan sulfate proteoglycans (HSPGs) and neuropilin co-receptors on the cell surface, enhancing their ability to bind and activate the VEGF receptors (VEGFRs). The term "VEGF" also encompasses VEGF receptors. There are three main subtypes of VEGFR, numbered 1, 2 and 3. Also, they may be membrane-bound (mbVEGFR) or soluble (sVEGFR), depending on alternative splicing.

Compounds

In one aspect, provided herein is a compound of Formula I:

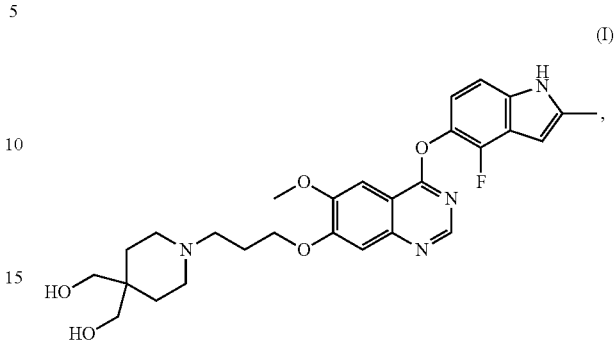

(I)

or a solvate, a hydrate, a polymorph, a co-crystal, a prodrug, an N-oxide, or an isotopically labeled compound thereof, or a pharmaceutically acceptable salt thereof.

In some embodiments, the compound is:

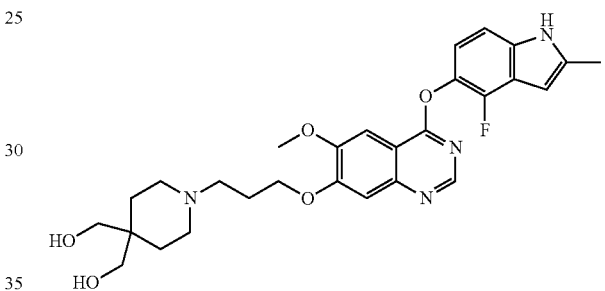

or a pharmaceutically acceptable salt thereof.

In some embodiments, the compound is:

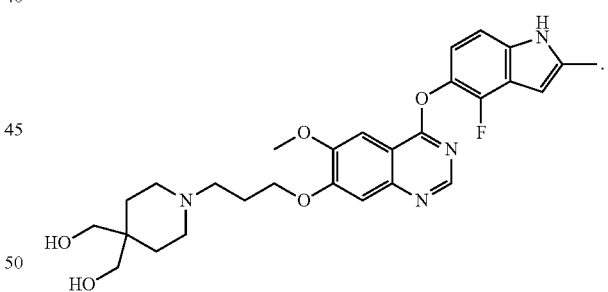

In some embodiments, the disclosure also is directed to isotopically labelled compounds of the afore-mentioned compounds or pharmaceutically acceptable salts thereof, which have the same structures as disclosed herein except that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^3$H)- and/or carbon-14 ($^{14}$C)-labelled compounds are particularly useful for various types of assays, such as substrate tissue distribution assays, due to relatively simple preparation and excellent detectability. For example, deuterium ($^2$H)-labelled ones are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2$H)-labelled ones or deuterated derivatives. In some specific embodiments, the isotope-labelled compounds and salts are deuterium ($^2$H)-labelled, wherein one or more hydrogen atoms therein have been replaced by deuterium. In chemical structures, deuterium is represented as "$^2$H" or "D."

The deuterium ($^2$H)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, Deuterium In Drug Discovery and Development, Ann. Rep. Med. Chem. 2011, 46, 403-417; and T. G. Gant "Using deuterium in drug discovery: leaving the label in the drug" J. Med. Chem. 2014, 57, 3595-3611, relevant portions of which are independently incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

One of ordinary skill in the art would understand that deuteration of one or more metabolically labile positions on a compound or active metabolite may lead to improvement of one or more superior DMPK properties while maintaining biological activity as compared to the corresponding hydrogen analogs. The superior DMPK property or properties may have an impact on the exposure, half-life, clearance, metabolism, and or even food requirements for optimal absorption of the drug product. Deuteration may also change the metabolism at other non-deuterated positions of the deuterated compound.

Compounds provided herein may be crystalline. In some embodiments, the compounds provided herein are monocrystalline. In some embodiments, the compounds provided herein are polycrystalline.

Compounds provided herein may also have a relatively low aqueous solubility (i.e. a low solubility in water, optionally with one or more buffers). For example, compounds provided herein may have an aqueous solubility of less than about or equal to about 3 mg/mL, less than about 1 mg/mL, less than about 0.3 mg/mL, less than about 0.1 mg/mL, less than about 0.03 mg/mL, less than about 0.01 mg/mL, less than about 1 µg/mL, less than about 0.1 µg/mL, less than about 0.01 µg/mL, less than about 1 ng/mL, less than about 0.1 ng/mL, or less than about 0.01 ng/mL at 25° C. In some embodiments, the compounds provided herein have an aqueous solubility of at least about 1 µg/mL, at least about 10 µg/mL, at least about 0.1 ng/mL, at least about 1 ng/mL, at least about 10 ng/mL, at least about 0.1 µg/mL, at least about 1 µg/mL, at least about 3 µg/mL, at least about 0.01 mg/mL, at least about 0.03 mg/mL, at least about 0.1 mg/mL, at least about 0.3 mg/mL, at least about 1.0 mg/mL, or at least about 3 mg/mL at 25° C. Combinations of the above-noted ranges are possible (e.g., an aqueous solubility of at least about 10 µg/mL and less than about 1 mg/mL). Other ranges are also possible. The compounds provided herein may have these or other ranges of aqueous solubility at any point throughout the pH range (e.g., at about pH 7 or from pH 1 to pH 14).

Compounds provided herein may be suitable for being processed into mucus-penetrating pharmaceutical compositions (e.g., particles or crystals). Mucus-penetrating pharmaceutical compositions have been described, at least, in U.S. Pat. No. 9,353,123 and US Patent Application Publication No. 2016-0235753, the entire contents of each of which are incorporated herein by reference.

In certain embodiments, the compounds provided herein are suitable for milling (e.g., nano-milling). In certain embodiments, the compounds provided herein are suitable for precipitation (e.g., microprecipitation, nanoprecipitation, crystallization, or controlled crystallization). In certain embodiments, the compounds provided herein are suitable for emulsification. In certain embodiments, the compounds provided herein are suitable for freeze-drying.

Compositions

In one aspect, provided herein are compositions, comprising a compound provided herein.

In some embodiments, the compound is a compound of Formula I:

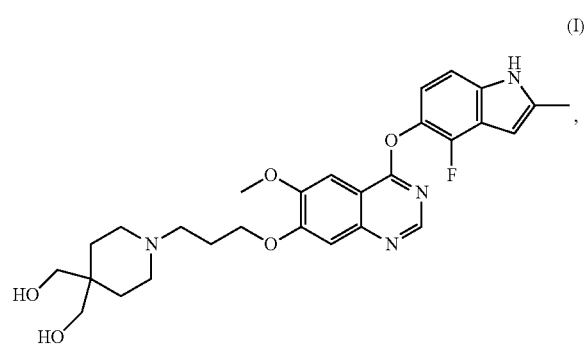 [SMILES: COc1cc2c(Oc3ccc4[nH]c(C)cc4c3F)ncnc2cc1OCCCN1CCC(CO)(CO)CC1]

(I)

or a solvate, a hydrate, a polymorph, a co-crystal, a prodrug, an N-oxide, or an isotopically labeled compound thereof, or a pharmaceutically acceptable salt thereof.

In some embodiments, the compound is:

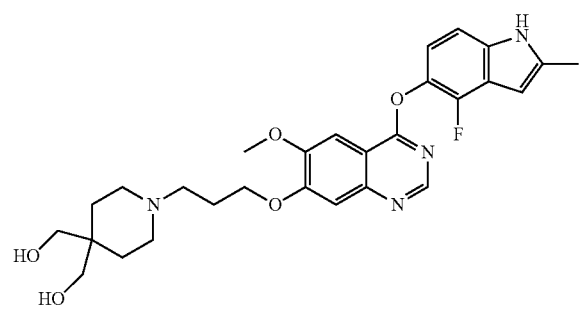 [SMILES: COc1cc2c(Oc3ccc4[nH]c(C)cc4c3F)ncnc2cc1OCCCN1CCC(CO)(CO)CC1]

or a pharmaceutically acceptable salt thereof.

In some embodiments, the compound is:

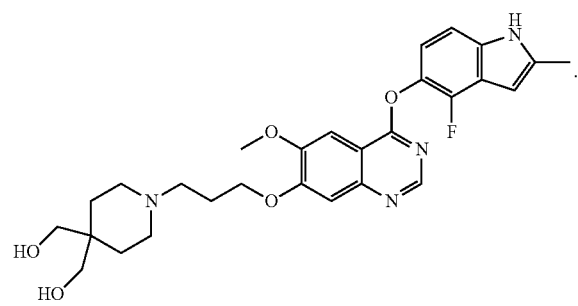 [SMILES: COc1cc2c(Oc3ccc4[nH]c(C)cc4c3F)ncnc2cc1OCCCN1CCC(CO)(CO)CC1]

In some embodiments, the composition further comprises a carrier.

In some embodiments, the composition is suitable for delivery to an eye of a subject.

Pharmaceutical Compositions

In one aspect, provided herein are pharmaceutical compositions, comprising a compound provided herein.

In some embodiments, the compound is a compound of Formula I:

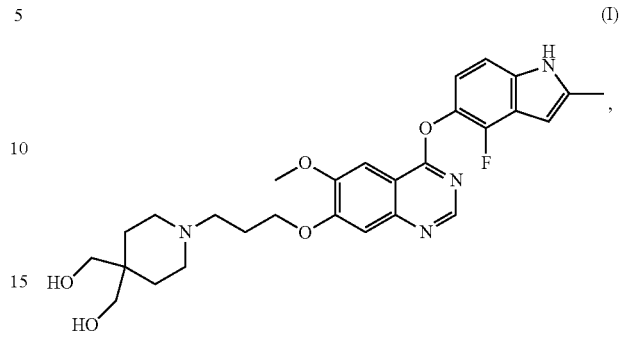

(I)

or a solvate, a hydrate, a polymorph, a co-crystal, a prodrug, an N-oxide, or an isotopically labeled compound thereof, or a pharmaceutically acceptable salt thereof.

In some embodiments, the compound is:

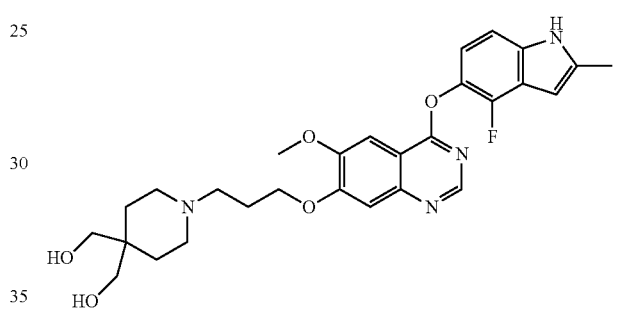

or a pharmaceutically acceptable salt thereof.

In some embodiments, the compound is:

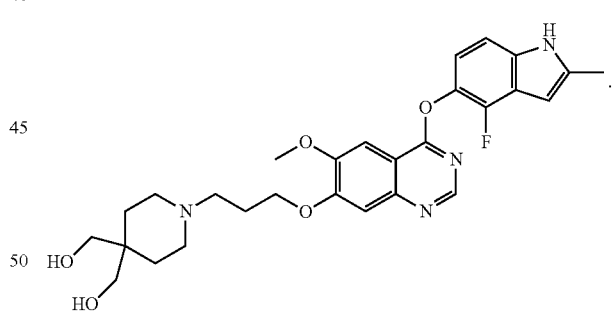

In some embodiments, the pharmaceutical composition further comprises a pharmaceutically acceptable carrier.

In some embodiments, the pharmaceutical composition is suitable for delivery to an eye of a subject.

Provided herein are pharmaceutical compositions comprising 7-(3-[4,4-bis(hydroxymethyl)-1-piperidinyl]propoxy)-4-(4-fluoro-2-methyl-1H-indol-5-yloxy)-6-methoxyquinazoline (Formula I) or a solvate, a hydrate, a polymorph, a co-crystal, a prodrug, an N-oxide, or an isotopically labeled compound thereof, or a pharmaceutically acceptable salt thereof, as provided herein, and optionally a pharmaceutically acceptable excipient. In certain embodiments, a provided composition comprises two or more compounds provided herein (e.g., a composition comprising at least two of a first pharmaceutically acceptable salt of Formula I, a second pharmaceutically acceptable salt of Formula I, or a compound of Formula I). In certain embodiments, a compound provided herein, or a pharmaceutically acceptable salt thereof, is provided in an effective amount in the pharmaceutical composition. In certain embodiments, the effective amount is a therapeutically effective amount. In certain embodiments, the effective amount is an amount effective for treating a disease. In certain embodiments, the effective amount is an amount effective for treating a growth factor-mediated disease. In certain embodiments, the effective amount is an amount effective for treating a VEGF-mediated disease. In certain embodiments, the effective amount is an amount effective for treating a VEGFR-mediated disease. In certain embodiments, the effective amount is an amount effective for treating a VEGFR2-mediated disease. In certain embodiments, the effective amount is an amount effective for treating a RET-mediated disease. In certain embodiments, the effective amount is a prophylactically effective amount. In certain embodiments, the effective amount is an amount effective to prevent a VEGF-mediated disease. In certain embodiments, the effective amount is an amount effective to prevent a VEGFR-mediated disease. In certain embodiments, the effective amount is an amount effective to prevent a VEGFR2-mediated disease. In certain embodiments, the effective amount is an amount effective to prevent a RET-mediated disease. In certain embodiments, the effective amount is an amount effective to treat an abnormal angiogenesis-associated disease such as atherosclerosis, hypertension, tumor growth, inflammation, rheumatoid arthritis, wet-form macular degeneration, dry-form macular degeneration, choroidal neovascularization, corneal neovascularization, retinal neovascularization, and diabetic retinopathy. In certain embodiments, the effective amount is an amount effective to treat cancer. In certain embodiments, the effective amount is an amount effective to treat macular degeneration (e.g., wet or dry age-related macular degeneration).

Pharmaceutical compositions provided herein can be prepared by any method known in the art of pharmacology. In general, such preparatory methods include the steps of bringing a compound provided herein (the "active ingredient") into association with a carrier or one or more other accessory ingredients, or both, and then, if necessary or desirable, shaping or packaging the product into a desired single-dose or multi-dose unit.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, about 10 mg to about 100 mg, or about 100 mg to about 1000 mg of a compound per unit dosage form.

Also provided herein are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kit further includes instructions for use.

In certain embodiments, the compounds, particles, pharmaceutical compositions, kits, and methods provided herein are useful for applications in the eye, such as treating or preventing an ocular disease (e.g., macular degeneration, dry eye syndrome, uveitis, allergic conjunctivitis, glaucoma, and rosacea).

Methods

Provided herein are compounds, particles, coated particles, and compositions thereof for treating a disease. In some embodiments, methods of treating a disease in a subject are provided which comprise administering an effective amount of a compound provided herein to a subject in need of treatment. In certain embodiments, the effective amount is a therapeutically effective amount. In certain embodiments, the effective amount is a prophylactically effective amount. In certain embodiments, the subject is suffering from a growth factor-associated disease. In certain embodiments, the subject is susceptible to a growth factor-associated disease. In certain embodiments, the subject is suffering from a RET-associated disease. In certain embodiments, the subject is susceptible to a RET-associated disease. In certain embodiments, the subject is at risk of developing macular degeneration.

Also provided herein are methods of inhibiting VEGF (e.g., VEGF-A, VEGF-B, VEGF-C, VEGF-D, VEGF-E, or a combination thereof) or VEGFR (e.g., VEGFR1, VEGFR2, VEGFR3, or a combination thereof) activity or signaling in a cell. In some embodiments, the VEGF is VEGF-A, VEGF-C, or VEGF-E. In some embodiments, the VEGFR is VEGFR2. Also provided herein are methods of inhibiting RET (a receptor tyrosine kinase that may be produced as three different isoforms: RET51, RET43, and RET9; RET is an abbreviation of "rearranged during transfection") activity or signaling in a cell. In some embodiments, such methods comprise contacting a cell with an effective amount of a compound provided herein. In some embodiments, the cell is in vitro. In some embodiments, the cell is in vivo.

In some embodiments, the present disclosure provides methods of treating a disease comprising contacting a biological sample with an effective amount of a compound provided herein. In certain embodiments, the biological sample includes a cell or tissue. In some embodiments, the methods comprise inhibiting growth factor signaling in a cell, tissue, or subject. In some embodiments, the biological sample is an ocular tissue. In certain embodiments, the method is an in vitro method. In certain embodiments, the method is an in vivo method. It will be understood by one of ordinary skill in the art that levels of inhibition are not necessary to be 100%. The levels of inhibition can be at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, or greater than 90% inhibition.

In some embodiments, the present disclosure provides methods to treat or prevent an ocular disease, i.e., a disease, ailment, or condition that affects or involves the eye or one or more of the parts or regions of the eye.

In some embodiments, the present disclosure provides a method to treat or prevent an ocular disease at the front of the eye of a subject. A front of the eye ocular disease includes post-surgical inflammation, uveitis, infections, aphakia, pseudophakia, astigmatism, blepharospasm, cataract, conjunctival diseases, conjunctivitis, corneal diseases, corneal ulcer, dry eye syndromes, eyelid diseases, lacrimal apparatus diseases, lacrimal duct obstruction, myopia, presbyopia, pupil disorders, corneal neovascularization, refractive disorders and strabismus. Glaucoma can be considered to be a front of the eye ocular condition in some embodiments because a clinical goal of glaucoma treatment can be to reduce a hypertension of aqueous fluid in the anterior chamber of the eye (i.e., reduce intraocular pressure).

In some embodiments, the present disclosure provides a method to target and/or treat portions within the posterior portion or back of the eye, such as the retina, the choroid, and/or the sclera, of a subject. In general, a back of the eye or posterior ocular disease is a disease, ailment, or condition which primarily affects or involves a tissue or fluid at the back of the eye, as provided herein. A posterior ocular disease can include a disease, ailment, or condition, such as intraocular melanoma, acute macular neuroretinopathy, Behçet's disease, choroidal neovascularization, uveitis, diabetic uveitis, histoplasmosis, infections, such as fungal or viral-caused infections, macular degeneration, such as acute macular degeneration, non-exudative age-related macular degeneration and exudative age related macular degeneration, edema, such as macular edema, cystoid macular edema and diabetic macular edema, multifocal choroiditis, ocular trauma which affects a posterior ocular site or location, ocular tumors, retinal disorders, such as central retinal vein occlusion, diabetic retinopathy (including proliferative diabetic retinopathy), proliferative vitreoretinopathy, retinal arterial occlusive disease, retinal detachment, uveitic retinal disease, sympathetic opthalmia, Vogt Koyanagi-Harada syndrome, uveal diffusion, a posterior ocular condition caused by or influenced by an ocular laser treatment, posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, retinoblastoma, and glaucoma. Glaucoma can be considered a posterior ocular condition in some embodiments because the therapeutic goal is to prevent the loss of or reduce the occurrence of loss of vision due to damage to or loss of retinal cells or optic nerve cells (i.e., neuroprotection). In some embodiments, the present disclosure provides a method to treat, or prevent glaucoma in a subject. In some embodiments, the present disclosure provides a method to treat, or prevent uveitis in a subject.

In some embodiments, the present disclosure provides a method to treat or prevent dry eye in a subject. In some embodiments, the compositions provided herein may address these issues by facilitating effective delivery of pharmaceutical agents to the appropriate tissues, promoting more even and/or wide-spread coverage across the eye surface, and/or avoiding or minimizing clearance of the pharmaceutical agent.

In some embodiments, the present disclosure provides a method to treat or prevent inflammation in the eye of a subject. Inflammation is associated with a variety of ocular diseases. Inflammation may also result from a number of ophthalmic surgical procedures, including cataract surgery.

In some embodiments, the present disclosure provides a method to treat or prevent macular degeneration in a subject. In some embodiments, the macular degeneration is age-related macular degeneration (AMD). AMD is a medical condition that typically affects older adults and results in a loss of vision in the center of the visual field (the macula) because of damage to the retina. It occurs in "dry" and "wet" forms. It is a major cause of blindness and visual impairment in older adults (>50 years). In the dry (nonexudative) form, cellular debris called drusen accumulate between the retina and the choroid, and the retina can become detached. In the wet (exudative) form, which is more severe, blood vessels grow up from the choroid behind the retina, and the retina can also become detached.

In certain embodiments, the compounds, particles, compositions, and/or formulations provided herein are packaged as a ready to use shelf stable suspension. Eye drop formulations are traditionally liquid formulations (solutions or suspensions) which can be packaged in dropper bottles (which dispense a standard drop volume of liquid) or in individual use droppers (typically used for preservative free drops, used once and disposed). These formulations are ready to use and can be self-administered. In some cases the bottle should be shaken before use to ensure homogeneity of the formulation, but no other preparation may be necessary. This may be the simplest and most convenient method of ocular delivery. The compositions and/or formulations provided herein can be packaged in the same way as traditional eye drop formulations.

In some embodiments, compounds provided herein are useful in treating proliferative diseases, ocular diseases, dermatological diseases, inflammatory diseases, autoimmune diseases, autoinflammatory diseases, and metabolic diseases.

In some embodiments, a provided compound is useful in treating a cancer. In some embodiments, provided herein are methods of treating cancer. In some embodiments, a provided compound is useful to delay the onset of, slow the progression of, or ameliorate the symptoms of cancer. In some embodiments, a provided compound is administered in combination with other compounds, drugs, or therapeutics to treat cancer.

In some embodiments, compounds provided herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor, head and neck cancer (e.g., head and neck squamous cell carcinoma, oral cancer (e.g., oral squamous cell carcinoma, throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (e.g., diffuse large B-cell lymphoma), follicular lymphoma, chronic lymphocytic leukemia/small lymphocytic lymphoma, mantle cell lymphoma, marginal zone B-cell lymphomas (e.g., mucosa-associated lymphoid tissue lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system lymphoma; and T-cell NHL such as precursor T-lymphoblastic lymphoma/leukemia, peripheral T-cell lymphoma (e.g., cutaneous T-cell lymphoma, mycosis fungiodes, Sézary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer, malignant hepatoma), lung cancer (e.g., bronchogenic carcinoma, small cell lung cancer, non-small cell lung cancer, adenocarcinoma of the lung), leiomyosarcoma, mastocytosis (e.g., systemic mastocytosis), myelodysplastic syndrome, mesothelioma, myeloproliferative disorder (e.g., polycythemia Vera, essential thrombocytosis, agnogenic myeloid metaplasia, a.k.a. myelofibrosis, chronic idiopathic myelofibrosis, chronic myelocytic leukemia, chronic neutrophilic leukemia, hypereosinophilic syndrome), neuroblastoma, neurofibroma (e.g., neurofibromatosis type 1 or type 2, schwannomatosis), neuroendocrine cancer (e.g., gastroenteropancreatic neuroendoctrine tumor, carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm, islet cell tumors), penile cancer (e.g., Paget's disease of the penis and scrotum), pinealoma, primitive neuroectodermal tumor, prostate cancer (e.g., prostate adenocarcinoma), rectal cancer, rhabdomyosarcoma, salivary gland cancer, skin cancer (e.g., squamous cell carcinoma, keratoacanthoma, melanoma, basal cell carcinoma), small bowel cancer (e.g., appendix cancer), soft tissue sarcoma (e.g., malignant fibrous histiocytoma, liposarcoma, malignant peripheral nerve sheath tumor, chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma, medullary thyroid cancer), urethral cancer, vaginal cancer and vulvar cancer (e.g., Paget's disease of the vulva), multiple endocrine neoplasia type 2A, multiple endocrine neoplasia type 2B, pheochromocytoma, and parathyroid hyperplasia.

In some embodiments, a provided compound is useful in treating a metabolic disease, such as diabetes or obesity. In some embodiments, a provided compound is useful to delay the onset of, slow the progression of, or ameliorate the symptoms of, diabetes. In some embodiments, the diabetes is Type 1 diabetes. In some embodiments, the diabetes is Type 2 diabetes. In some embodiments, a provided compound is useful to delay the onset of, slow the progression of, or ameliorate the symptoms of, obesity. In some embodiments, a provided compound could be used in combination with other compounds, drugs, or therapeutics, such as metformin and insulin, to treat diabetes and/or obesity.

In one aspect, provided herein are methods of treating an ocular disease in a subject in need thereof, comprising administering to the subject a therapeutically effective amount of a compound of Formula I:

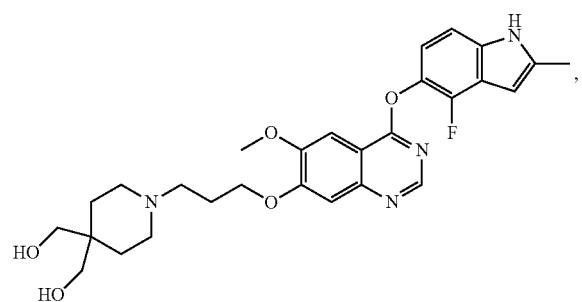

(I)

or a solvate, a hydrate, a polymorph, a co-crystal, a prodrug, an N-oxide, or an isotopically labeled compound thereof, or a pharmaceutically acceptable salt thereof.

In one aspect, provided herein are methods of treating an ocular disease in a subject in need thereof, comprising administering to the subject a therapeutically effective amount of a compound of Formula I:

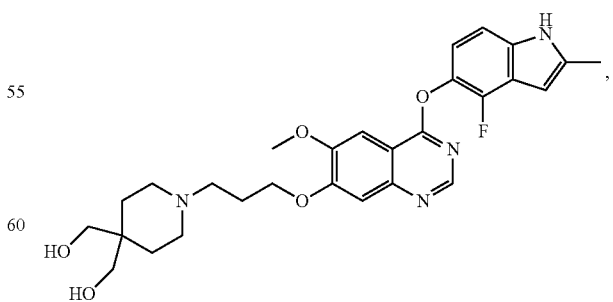

(I)

or a pharmaceutically acceptable salt thereof.

In one aspect, provided herein are methods of treating an ocular disease in a subject in need thereof, comprising administering to the subject a therapeutically effective amount of a compound of Formula I:

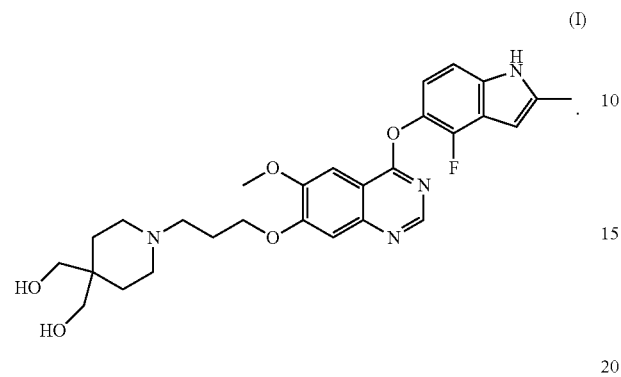

(I)

In another aspect, provided herein are methods of treating an ocular disease in a subject in need thereof, comprising administering to the subject a therapeutically effective amount of a composition comprising a compound of Formula I:

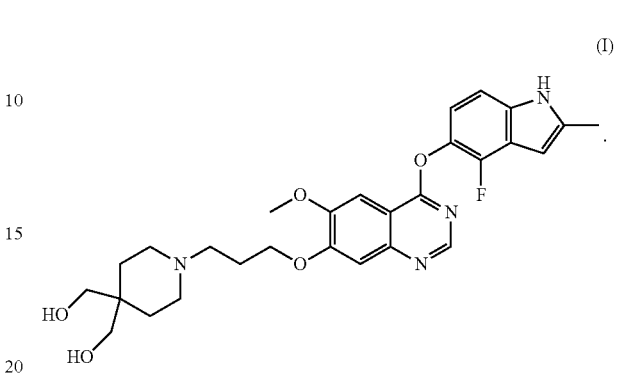

(I)

In another aspect, provided herein are methods of treating an ocular disease in a subject in need thereof, comprising administering to the subject a therapeutically effective amount of a composition comprising a compound of Formula I:

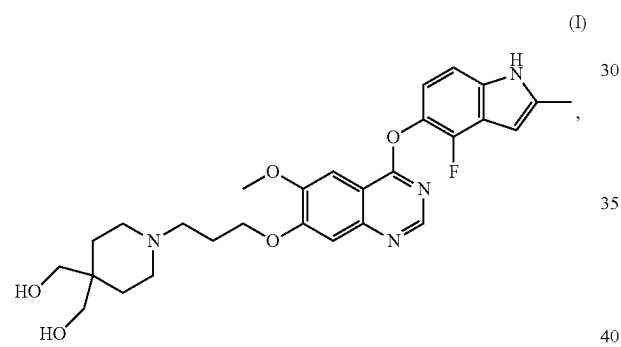

(I)

In another aspect, provided herein are methods of treating an ocular disease in a subject in need thereof, comprising administering to the subject a therapeutically effective amount of a pharmaceutical composition comprising a compound of Formula I:

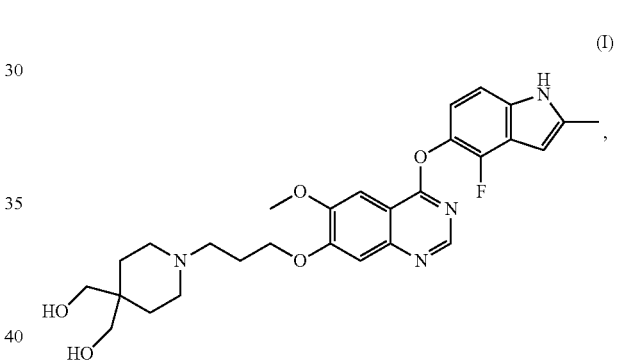

(I)

or a solvate, a hydrate, a polymorph, a co-crystal, a prodrug, an N-oxide, or an isotopically labeled compound thereof, or a pharmaceutically acceptable salt thereof.

In another aspect, provided herein are methods of treating an ocular disease in a subject in need thereof, comprising administering to the subject a therapeutically effective amount of a composition comprising a compound of Formula I:

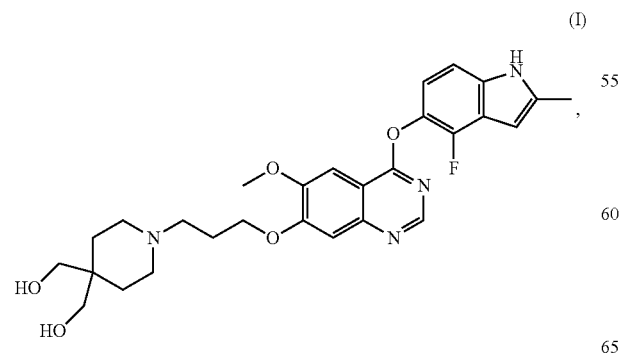

(I)

or a pharmaceutically acceptable salt thereof.

or a solvate, a hydrate, a polymorph, a co-crystal, a prodrug, an N-oxide, or an isotopically labeled compound thereof, or a pharmaceutically acceptable salt thereof.

In another aspect, provided herein are methods of treating an ocular disease in a subject in need thereof, comprising administering to the subject a therapeutically effective amount of a pharmaceutical composition comprising a compound of Formula I:

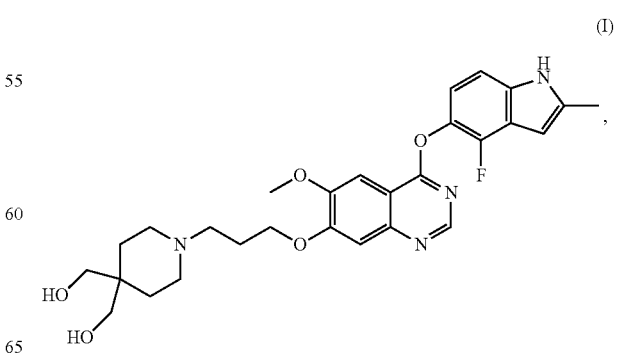

(I)

or a pharmaceutically acceptable salt thereof.

In another aspect, provided herein are methods of treating an ocular disease in a subject in need thereof, comprising administering to the subject a therapeutically effective amount of a pharmaceutical composition comprising a compound of Formula I:

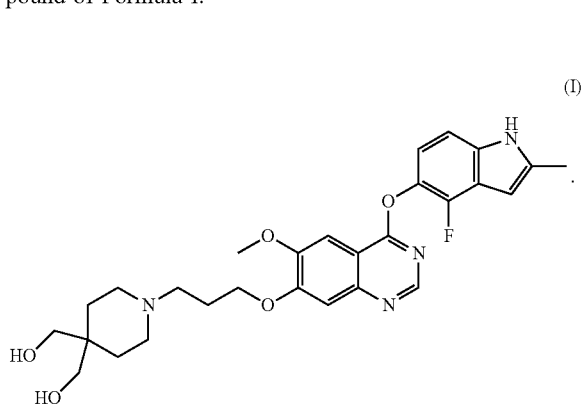

(I)

In some embodiments of the methods provided herein, the composition further comprises a carrier.

In some embodiments of the methods provided herein, the pharmaceutical composition further comprises a pharmaceutically acceptable carrier.

In some embodiments of the methods provided herein, the compound is:

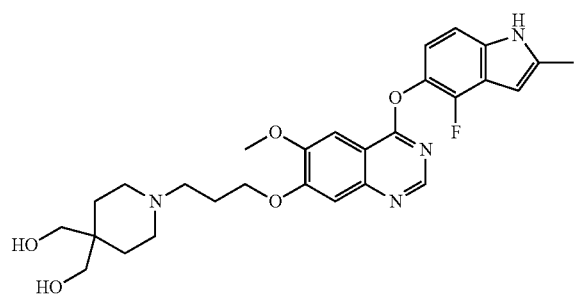 [SMILES: COc1cc2c(Oc3ccc4[nH]c(C)cc4c3F)ncnc2cc1OCCCN1CCC(CO)(CO)CC1]

or a solvate, a hydrate, a polymorph, a co-crystal, a prodrug, an N-oxide, or an isotopically labeled compound thereof, or a pharmaceutically acceptable salt thereof.

In some embodiments of the methods provided herein, the compound is:

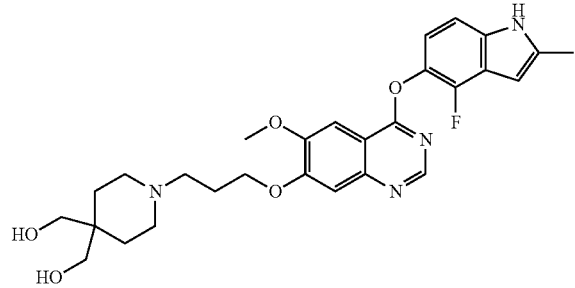 [SMILES: COc1cc2c(Oc3ccc4[nH]c(C)cc4c3F)ncnc2cc1OCCCN1CCC(CO)(CO)CC1]

or a pharmaceutically acceptable salt thereof.

In some embodiments of the methods provided herein, the compound is:

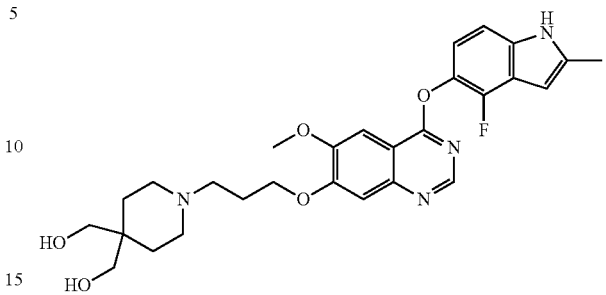

In some embodiments of the methods provided herein, the ocular disease is a retinopathy.

In some embodiments of the methods provided herein, the ocular disease is macular degeneration.

In some embodiments of the methods provided herein, the ocular disease is glaucoma.

In some embodiments of the methods provided herein, the ocular disease is corneal vascularization.

In some embodiments of the methods provided herein, the compound, composition, or pharmaceutical composition is delivered to one eye or two eyes of the subject.

In some embodiments of the methods provided herein, the compound, composition, or pharmaceutical composition is delivered to an eye of the subject.

In some embodiments of the methods provided herein, the compound, composition, or pharmaceutical composition is delivered to two eyes of the subject.

In another aspect, provided herein are methods of preparing a compound of Formula (I),

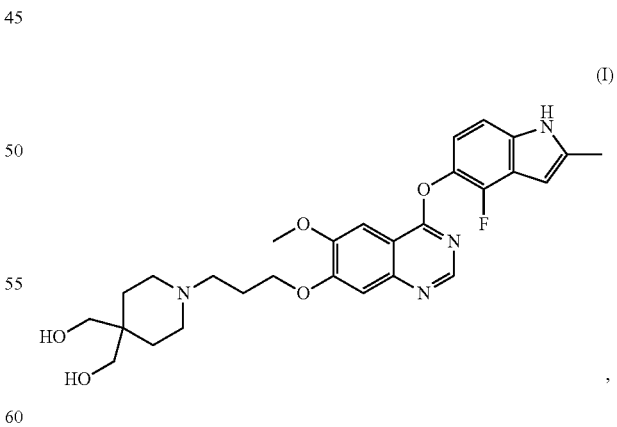

(I)

or a solvate, a hydrate, a polymorph, a co-crystal, a prodrug, an N-oxide, or an isotopically labeled compound thereof, or a pharmaceutically acceptable salt of any of the foregoing.

In some embodiments, the method comprises: contacting a compound of Formula (X),

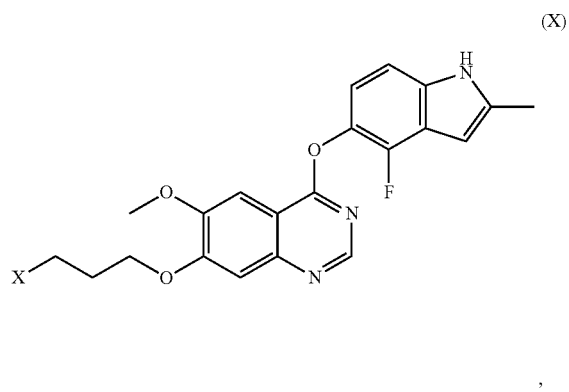

(X)

or a salt thereof, or an isotopically labeled compound (e.g., deuterated derivative) of any of the foregoing,
wherein X is a halogen,
with a compound of Formula (Y),

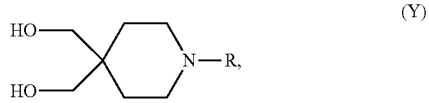

(Y)

or a salt thereof, or an isotopically labeled compound (e.g., deuterated derivative) of any of the foregoing,
wherein R is an amine protecting group, to form a compound of Formula (I)

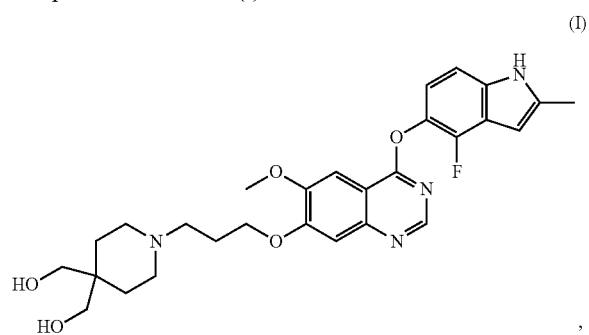

(I)

or a solvate, a hydrate, a polymorph, a co-crystal, a prodrug, an N-oxide, or an isotopically labeled compound thereof, or a pharmaceutically acceptable salt of any of the foregoing.

Any suitable conditions known in the art for a nucleophilic reaction of an amine can be used.

In some embodiments, contacting a compound of Formula (X) or a salt thereof, or a deuterated derivative of any of the foregoing, with a compound of Formula (Y) or a salt thereof, or an isotopically labeled compound (e.g. a deuterated derivative) of any of the foregoing is performed under a basic condition in the presence of a base. In some embodiments, the base is a metal carbonate or a metal hydroxide. In some embodiments, the base is a metal carbonate. In some embodiments, the base is $Na_2CO_3$ or $K_2CO_3$.

In some embodiments, X of Formula (X) is Cl or F. In some embodiments, X of Formula (X) is Cl.

Any suitable amine protecting group can be used for R of Formula (Y). In some embodiments, the amine protecting group is Fmoc (9-fluorenylmethyloxycarbonyl), Boc (tert-Butyloxycarbonyl), p-nitrophenyl, carbobenzyloxy (Cbz), p-methoxybenzyl carbonyl (Moz or MeOZ), acetyl (Ac), benzoyl (Bz), benzyl (Bn), p-methoxybenzyl (PMB), 3,4-dimethozybenzyl (DMPM), p-methoxyphenyl (PMP), tosyl (Ts), tricholorethyl chloroformate (Troc), a carbamate, or a sulfonamide group. In some embodiments, R of Formula (Y) is tert-Butyloxycarbonyl.

EXAMPLES

Example 1: Synthesis of 7-(3-[4,4-bis(hydroxymethyl)-1-piperidinyl]propoxy)-4-(4-fluoro-2-methyl-1H-indol-5-yloxy)-6-methoxyquinazoline (Compound 1)

Scheme 1

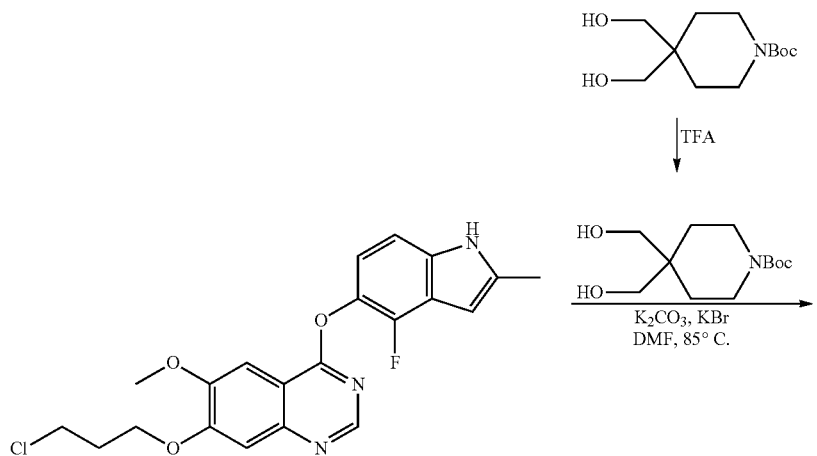

-continued

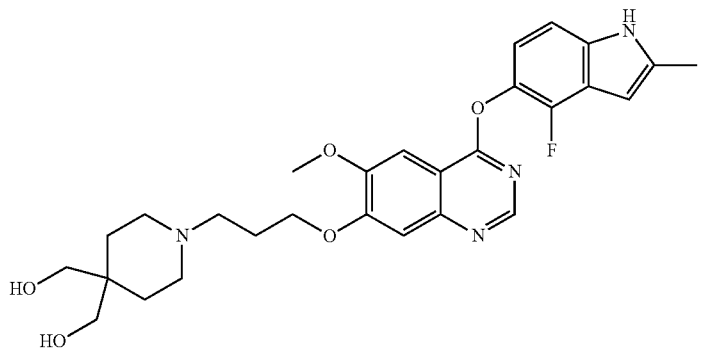

Tert-butyl 4,4-bis(hydroxymethyl)piperidine-1-carboxylate (400 mg, 1.63 mmol) was dissolved in trifluoroacetic acid (10 mL). After 30 minutes the solvent was evaporated. Dichloromethane (25 mL) was added, the solvent was evaporated and the colorless oily residue was stirred under high vacuum for 30 min. N,N-dimethylformamide (10 mL) was added followed by 7-(3-chloropropoxy)-4-(4-fluoro-2-methyl-1H-indol-5-yloxy)-6-methoxyquinazoline (200 mg, 0.48 mmol), potassium bromide (200 mg, 1.69 mmol) and potassium carbonate (1.0 g, 7.24 mmol). The suspension was heated to 85° C. and stirred for 6 hours. The solvent was evaporated and the residue was partitioned between ethyl acetate (100 mL) and brine (20 mL). The organic solution was dried with anhydrous magnesium sulfate, filtered and evaporated leaving thick brown oil. The oil was dissolved in a minimal amount of ethyl acetate and applied on a silica pad (about 10 g). The impurities were eluted with ethyl acetate: methanol (80:20) and the compound was eluted with ethyl acetate:methanol:conc. ammonium hydroxide (66:17:17). The solvent was evaporated and the residue was dissolved in ethyl acetate (50 mL) and washed with brine (2 mL). The organic solution was dried with anhydrous magnesium sulfate, filtered and evaporated to about a 10 mL volume. Trituration with hexane and sonication produced a precipitate, which was filtered off and dried in high vacuum to yield 80 mg of Compound 1 as a white solid. LCMS: 5.88 min, 526.2 (M+2, 20%), 525.2 (M+I, 30%), 263.2 (25%), 157.2 (100%) (positive ionization mode); 524.2 (M, 10%), 523.2 (M−1, 30%), 249.0 (15%), 113.0 (100%) (negative ionization mode).

Example 2: VEGFR2 and RET9 Binding Assay

A competition binding assay (DISCOVERX™ KINOMESCAN™) was used to measure the ability of a compound to compete for binding of an immobilized adenosine triphosphate (ATP) site directed ligand using a DNA-tagged vascular endothelial growth receptor 2 (VEGFR2) as the target. The ability of the test compound to compete with the immobilized ligand was measured using quantitative polymerase chain reaction (qPCR) of the DNA tag (Fabian, M. A. et al., 23 *Nature Biotechnology* 329-336 (2005); Karaman, M. W. et al., 26 *Nature Biotechnology* 127-132 (2008)).

A VEGFR2 tagged T7 phage strain was prepared in an *Escherichia coli* (*E. coli*) derived from the BL21 strain. The *E. coli* were grown to log-phase, infected with VEGFR2 tagged T7 phage and then incubated with shaking at 32° C. until lysis. The lysate containing the kinase was then centrifuged and filtered to remove cell debris. Affinity resin for the VEGFR2 assay was prepared by treating Streptavidin-coated magnetic beads with a biotinylated small molecule ligand for 30 minutes at room temperature. The beads were blocked with excess biotin and then washed with blocking buffer (SEABLOCK (PIERCE), 1% bovine serum albumin, 0.17% phosphate buffered saline, 0.05% TWEEN 20, 6 mM dithiothreitol). The binding reaction was initiated by combining in a well of a polystyrene 96-well plate, DNA tagged VEGFR2, liganded affinity beads and the serial diluted test compound in 1× binding buffer (20% SEABLOCK, 0.17× phosphate buffered saline, 0.05% TWEEN 20, 6 mM dithiothreitol) in a final volume of 0.135 ml. The assay plates were incubated at room temperature with shaking for 1 hour and then the beads were washed with wash buffer (1× phosphate buffered saline, 0.05% TWEEN 20). The beads were re-suspended in elution buffer (1× phosphate buffered saline, 0.05% TWEEN 20, 0.05 µM non-biotinylated affinity ligand) and incubated at room temperature with shaking for 30 minutes. The VEGFR2 concentration in the eluate was measured using qPCR.

An 11-point dose response curve of 3-fold serial diluted test compound starting at 1 µM was used to determine the VEGFR2 dissociation constant ($K_d$). The compounds were prepared in 100% DMSO at 100× the final test concentration and the diluted to 1× in the assay for final DMSO concentration of 1%. Binding constants were calculated with standard dose-response curve using the Hill equation with Hill slope set to −1. Curves were fit using a non-linear least square fit with the Levenberg-Marquardt algorithm.

TABLE 1

VEGFR2 $K_d$ values of selected compounds.

| Compound ID | $K_d$ |
|---|---|
| 1 | 0.38 nM |

Similarly, a competition binding assay (DISCOVERX™ KINOMESCAN™) was used to determine the dissociation constant (Kd) of Compound 1 to RET9.

TABLE 2

RET9 $K_d$ values of selected compounds.

| Compound ID | $K_d$ |
|---|---|
| 1 | 3.9 nM |

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A compound, wherein the compound is: a compound of Formula I:

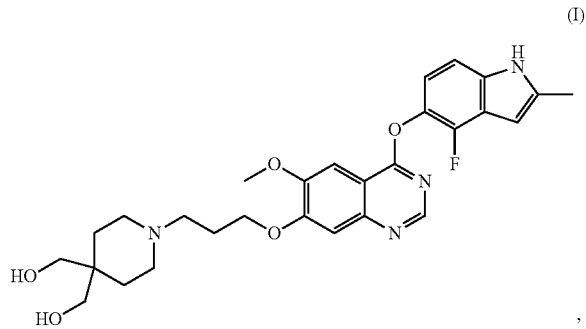 [SMILES: COc1cc2c(Oc3ccc4[nH]c(C)cc4c3F)ncnc2cc1OCCCN1CCC(CO)(CO)CC1]

or a pharmaceutically acceptable salt thereof.

2. The compound of claim 1, wherein the compound is:

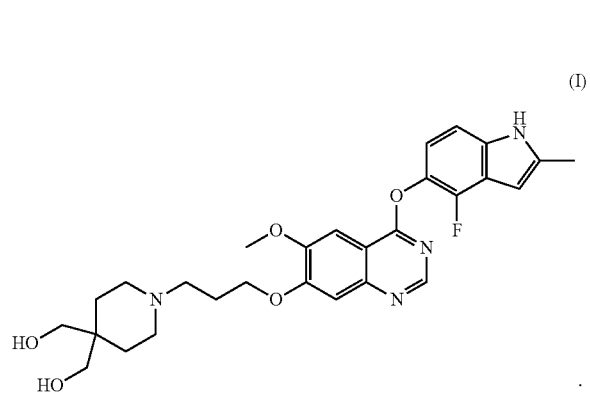 [SMILES: COc1cc2c(Oc3ccc4[nH]c(C)cc4c3F)ncnc2cc1OCCCN1CCC(CO)(CO)CC1]

3. The compound of claim 1, wherein the compound is a pharmaceutically acceptable salt of

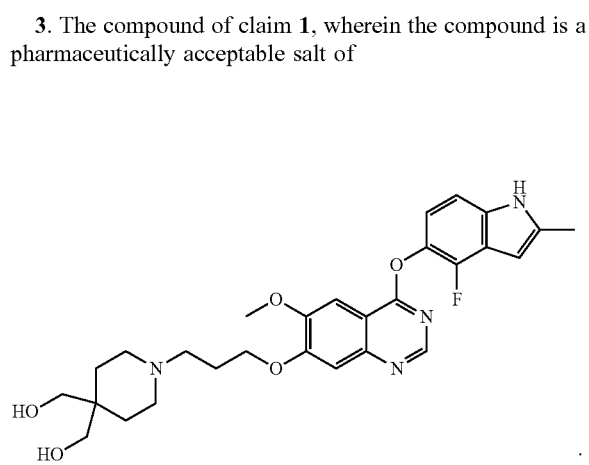

4. A pharmaceutical composition, comprising the compound of claim 1, or a pharmaceutically acceptable salt thereof and a pharmaceutically acceptable carrier.

5. The pharmaceutical composition of claim 4, wherein the composition is suitable for delivery to an eye of a subject.

6. A method of preparing a compound of Formula (I),

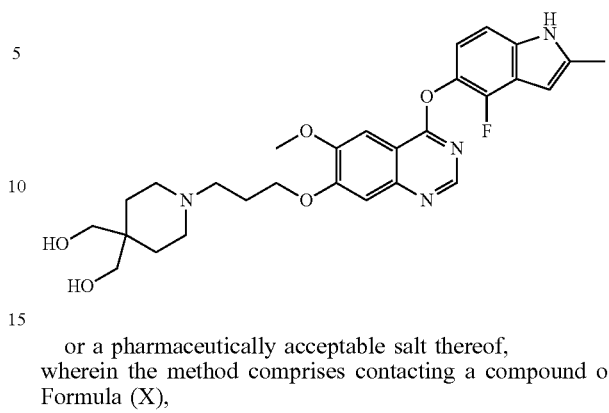

or a pharmaceutically acceptable salt thereof,
wherein the method comprises contacting a compound of Formula (X),

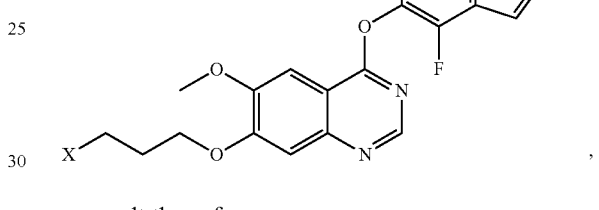

or a salt thereof,
wherein X is a halogen,
with a compound of Formula (Y),

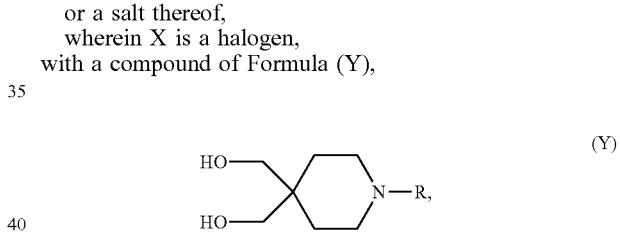

or a salt thereof,
wherein R is an amine protecting group,
to form the compound of Formula (I), or a pharmaceutically acceptable salt thereof.

7. The method of claim 6, wherein X is Cl or F.

8. The method of claim 6, wherein R is tert-Butyloxycarbonyl.

* * * * *